(12) United States Patent
Vacher et al.

(10) Patent No.: US 7,776,901 B2
(45) Date of Patent: Aug. 17, 2010

(54) IMIDAZOLIC COMPOUNDS AND USE THEREOF AS ALPHA-2 ADRENERGIC RECEPTORS

(75) Inventors: Bernard Vacher, Castres (FR); Bernard Bonnaud, Lagarrigue (FR); Marc Marien, Castres (FR); Peter Pauwels, Chessenaz (FR)

(73) Assignee: Pierre Fabre Medicament, Boulogne (FR)

( * ) Notice: Subject to any disclaimer, the term of this patent is extended or adjusted under 35 U.S.C. 154(b) by 78 days.

(21) Appl. No.: 11/783,079

(22) Filed: Apr. 5, 2007

(65) Prior Publication Data

US 2007/0197793 A1    Aug. 23, 2007

Related U.S. Application Data

(63) Continuation of application No. 10/514,487, filed as application No. PCT/FR03/01476 on May 15, 2003, now Pat. No. 7,220,866.

(30) Foreign Application Priority Data

May 16, 2002    (FR)    .................... 02 06026

(51) Int. Cl.
    *A61K 31/4164*    (2006.01)
(52) U.S. Cl. ..................................... 514/396
(58) Field of Classification Search ............ 514/396
    See application file for complete search history.

(56) References Cited

U.S. PATENT DOCUMENTS

2002/0013356 A1    1/2002    Ratilainen et al.

FOREIGN PATENT DOCUMENTS

WO        01/85698 A1    11/2001

OTHER PUBLICATIONS

Memory Loss [online] [retrieved on Sep. 4, 2008] [URL; http://www.nlm.nih.gov/medlineplus/ency/article/003257.htm].*
Vippagunta, et al. Advanced Drug Delivery Reviews 48 (2001) 3-26.*
Isomers [online], [retrieved on Mar. 11, 2007]. Retrieved from internet, URL; http://chemed.chem.purdue.edu/genchem/topicreview/bp/1organic/isomers.html>.*
Huntington's diseas [online] retrieved on Sep. 10, 2009 from the internet, (<URL:http://www.healthline.com/adamcontent/huntingtons-disease>).*
Cecil Textbook of Medicine, 20th Edition (1996), vol. 2, pp. 2050-2057.
Cecil Textbook of Medicine, 20th Edition (1996), vol. 2, pp. 1992-1996.
FDA mulls drugs to slow late-stage Alzheimer's[online], [retrieved on Sep. 23, 2003]. Retrieved from the Internet, URL; http://www.cnn.com/2003/HEALTH/conditions/09/24/alzheimers.drug.ap/index.html>.
Neurodegenerative disease [online], [retrieved on Jul. 21, 2006]. Retrieved from the Internet, URL; http://en.wikipedia.org/wiki/Neurodegenerative_disease>.

* cited by examiner

*Primary Examiner*—Rebecca L Anderson
*Assistant Examiner*—Shawquia Young
(74) *Attorney, Agent, or Firm*—Buchanan Ingersoll & Rooney PC

(57) ABSTRACT

The invention provides methods of treating a memory deficiency in a subject in need of such treatment, where the methods comprise administering to a subject an effective amount of a compound of formula (1):

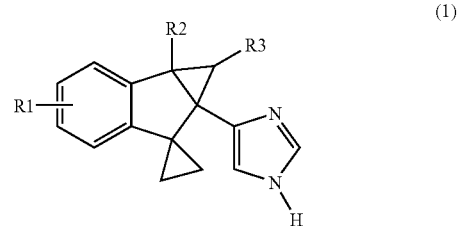

wherein: R1 is hydrogen, fluorine or a methoxyl group, R1 being in position 2, 3, 4 or 5 of the aromatic carbocycle; R2 is hydrogen or a methyl group; R3 is hydrogen, a methyl group or an ethyl group; and their pharmaceutically acceptable acid addition salt as well as the isomers and the tautomers thereof. The memory deficiency may be correlated with a memory deficiency induced by scopolamine.

13 Claims, No Drawings

IMIDAZOLIC COMPOUNDS AND USE THEREOF AS ALPHA-2 ADRENERGIC RECEPTORS

CROSS-REFERENCE TO EARLIER APPLICATIONS

This application is a continuation application of U.S. application Ser. No. 10/514,487, filed on Sep. 22, 2005, now allowed, which was the National Stage of International Application No/PCT/FR03/01476, filed May 15, 2003, and claims priority under 35 U.S.C. §119(a)-(d) of French Patent Application No. 02/06026, filed May 16, 2002, said applications being incorporated by reference herein in their entireties and relied upon.

The present invention relates to new imidazolic compounds. The derivatives according to the invention interact selectively with pre and/or post-synaptic alpha-2 type adrenergic receptors (J. Neurochem. 2001, 78, 685-93) on which they behave as partial agonists, antagonists or reverse agonists. As such, the compounds according to the invention are therefore potentially useful in the treatment of diseases or conditions susceptible to adrenergic regulation controlled by alpha-2 adrenergic receptors. The list of diseases considered as susceptible to such regulation is excessively long. However, the scope of the present invention is restricted to the treatment of neurodegenerative diseases and the treatment of the progression thereof (Psychopharmacology 1996, 123(3), 239-49; Prog. Neuro-Psychopharmacol. Biol. Psychiatry 1999, 23(7), 1237-46; U.S. Pat. No. 5,663,167; FR 2789681; WO 9835670; WO 9806393; WO 9500145; WO 9413285; WO 9118886), particularly the treatment of Alzheimer's disease or the treatment of the progression thereof (U.S. Pat. No. 5,281,607; FR 2795727; WO 9501791; WO 9415603).

Alzheimer's disease is the most widespread progressive degenerative disease in the elderly population. It is estimated that over 15 million people are affected (New Engl. J. Med. 1999, 341(22), 1670-79; Drug Benefit Trends 2001, 13/7, 27-40). Acetylcholinesterase inhibitors (e.g. tacrine, donepezil, rivastigmine and galantamine) represent, at the present time, the only symptomatic treatment of this disease. However, the therapeutic benefits obtained are modest at the very mode (Drugs 2001, 61/1, 41-52). Since effective therapeutic strategies against Alzheimer's disease are limited (Curr. Opin. Invest. Drugs 2001, 2(5), 645-56), the discovery of new treatments using molecules with a different mode of action to that of the molecules currently available in clinical practice and capable of treating or delaying the progression of the disease is therefore highly desirable.

It has been demonstrated, in vitro and on animals, that a substance activating the noradrenergic system may, firstly, inhibit the progression of neuronal degeneration (J. Neurophysiol. 1998, 79(6), 2941-63; Pharmacol. Biochem. Behav. 1997, 56(4), 649-55; J. Cereb. Blood Flow Metabolism 1990, 10(6), 885-94) and, secondly, stimulate neuronal growth (J. Comp. Neurol. 1974, 155(1), 15-42; Neuroscience 1979, 4(11), 1569-82; Neuroreport 1991, 2, 528-8). As a result, compounds with partial agonistic, antagonistic or reverse antagonistic properties on alpha-2 adrenergic receptors, particularly on pre-synaptic alpha-2 receptors, may be useful in the treatment of neurodegenerative diseases. In view of the therapeutic potential of compounds with partial agonistic, antagonistic or reverse antagonistic properties for alpha-2 adrenergic receptors, the discovery of new structures having such properties is highly desirable. As such, the applicant discovered that new imidazolic derivatives interact selectively with alpha-2 subtype adrenergic receptors on which they behave as partial agonists, antagonists or reverse agonists.

Numerous pre and/or post-synaptic antagonists and/or partial agonists of alpha-2 adrenergic receptors are known and described in the literature. Although the compounds in questions belong to different chemical classes (Idrugs 2001, 4(6), 662-76), some comprise a common 1H-imidazole type structural unit in their chemical structure. For example, the latter include compounds such as:

4-(1-indanylalkyl)-(WO 1051472);
4-(benzothienyl)-(WO 9951593);
dihydro-indole-(FR 2735776);
dihydro-indenyl-(EP 247764);
4-(5-fluoro-2,3-dihydro-1H-inden-2-yl)-(WO 9500492);
4(5)-(2-ethyl-2,3-dihydro-2-silainden-2-yl)-(Eur. J. Med. Chem. 1996, 31(9), 725-9;
thieno[3,4-c]pyrroles (EP 599697);
4-(2-aryl- and -cycloalkyl-3,3,3-trifluoropropyl)-(EP 486385);
4-substitute-imidazole (J. Med. Chem. 1992, 35(4), 750-5);
4(5)-(2,2-diphenylethyl)-(Eur. J. Med. Chem. 1990, 25(7), 557-68);
imidazole derivative (GB 2225782; EP 183492 and WO 9313074);
4-(5-fluoro-2,3-dihydro-1H-inden-2-yl)-(WO 9500492).

Of the compounds mentioned above, some only comprise relatively minimal structural differences. The most similar state of the art is represented by polycyclic indanylimidazole type compounds, claimed in the patent WO 0185698, complying with formula a below:

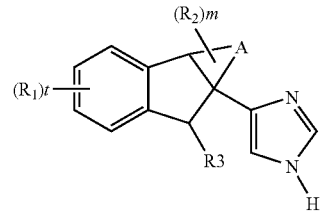

formula a wherein, among others:
A may form, with the two carbon atoms whereby it is attached, a 3-chain carbon-containing mono-cycle;
m may be 0 or 1;
R2 may be a (C1-6)alkyl group
t may be 0 or 1;
t is 1 and R1 may be a halogen or a (C1-6)alkyloxy group;
R3 may be a hydrogen, OH, =O, (C1-6)alkyl or (C1-6) alkyloxy.

Therefore, the compounds represented above and the compounds according to the present invention are differentiated in the nature of the substitutent in position 4 of the imidazole group, particularly by the presence of a 6-spiro-cyclopropane structural unit in the compounds according to the invention. Many structures comprising a 1H-imidazole group substituted in position 4 are already known for these alpha-2 adrenergic properties (see above). However, surprisingly, it appears that the substitutent 6-spiro-1'-cyclopropane-1a,6-dihydro-1H-cyclopropa[a]inden-6a-yl gives the compounds according to the invention a very specific pharmacological profile.

In fact, we have demonstrated, in vitro:
an affinity of the compounds according to the invention with respect to the human alpha-2A subtype, antagonistic or reverse agonistic properties of the compounds according to the invention on alpha-2A receptors.

In addition, we have demonstrated, in vivo, that the products according to the invention are capable of inhibiting the effect of scopolamine in a memory deficiency test. This test is considered as a representative animal model of the memory disorders arising in the course of Alzheimer's disease (Psychopharmacology 1992, 106, 26-30; Eur. J. Clin. Invest. 1998, 28, 944-9; Exp. Neurol. 2000, 163, 495-529). The compounds according to the invention, having such an activity profile, are therefore potentially useful for the treatment of diseases or disorders susceptible to the action of partial agonists, antagonists or reverse agonists of alpha-2 adrenergic receptors, particularly for the treatment of neurodegenerative diseases for which a significant therapeutic requirement exists.

Finally, the preparation method of the compounds according to the invention is different, that of the compounds claimed in the patient WO 0185698.

More specifically, the present invention relates to new 4-(6-spiro-1'-cyclopropane-1a,6-dihydro-1H-cyclopropa[a]inden-6a-yl)-1H-imidazole derivatives which, in their basic form, comply with the general formula 1:

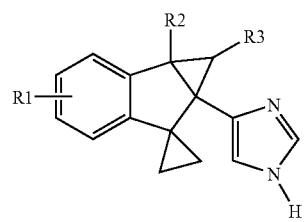

(1)

wherein:
R1 represents a hydrogen atom, a fluorine atom or a methoxyl group (OCH$_3$), the substitutent R1 on the aromatic carbocycle possibly occupying the position 2, 3, 4 or 5;
R2 represents a hydrogen atom or a methyl group;
R3 represents a hydrogen atom, a methyl group or an ethyl group;

their addition salts and, if applicable, addition salt hydrates with pharmaceutically acceptable mineral acids or organic acids along with their tautomeric forms, enantiomers and enantiomer mixtures and stereoisomers, pure or in racemic mixtures or not.

In a particular embodiment of the invention, the compounds according to formula 1 wherein:
R1 and R2 have the same significance as above;
R3 represents a methyl group or an ethyl group;
the preferential stereoisomers of the products according to the invention are those wherein the R3 and 1H-imidazole substitutents occupy either anti-periplanar positions or syn-periplanar positions with reference to the plane defined by the cyclopropanic nucleus.

The term anti-periplanar is used by the inventors to refer to the relative configurations of the molecules 1 for which the R3 and 1H-imidazole substitutents are located on either side of the plane defined by the cyclopropanic nucleus. The term syn-periplanar is used by the inventors to refer to the relative configurations of the molecules 1 for which the R3 and 1H-imidazole substitutents are located on the same side of the plane defined by the cyclopropanic nucleus.

The compounds according to the general formula 1 may exist in several tautomeric forms. Such tautomeric forms, although they are not explicitly reported in the present application to simplify the graphic representation of the developed formulas, are nevertheless included in the scope of the invention. The compounds according to the invention comprise several asymmetrical carbon atoms in their structure. For this reason, they exist in the form of enantiomers and diastereoisomers. The invention relates equally well to each pure stereoisomer, i.e. associated with less than 5% of another stereoisomer or a mixture of other stereoisomers, and mixtures of one or more stereoisomers in all proportions. Therefore, the compounds according to the invention may be used as pure stereoisomers or racemic or non-racemic stereoisomer mixtures.

Finally, the invention relates to the preparation method of derivatives according to general formula 1.

The derivatives according to general formula 1 may be obtained using the method described in the reaction diagram below.

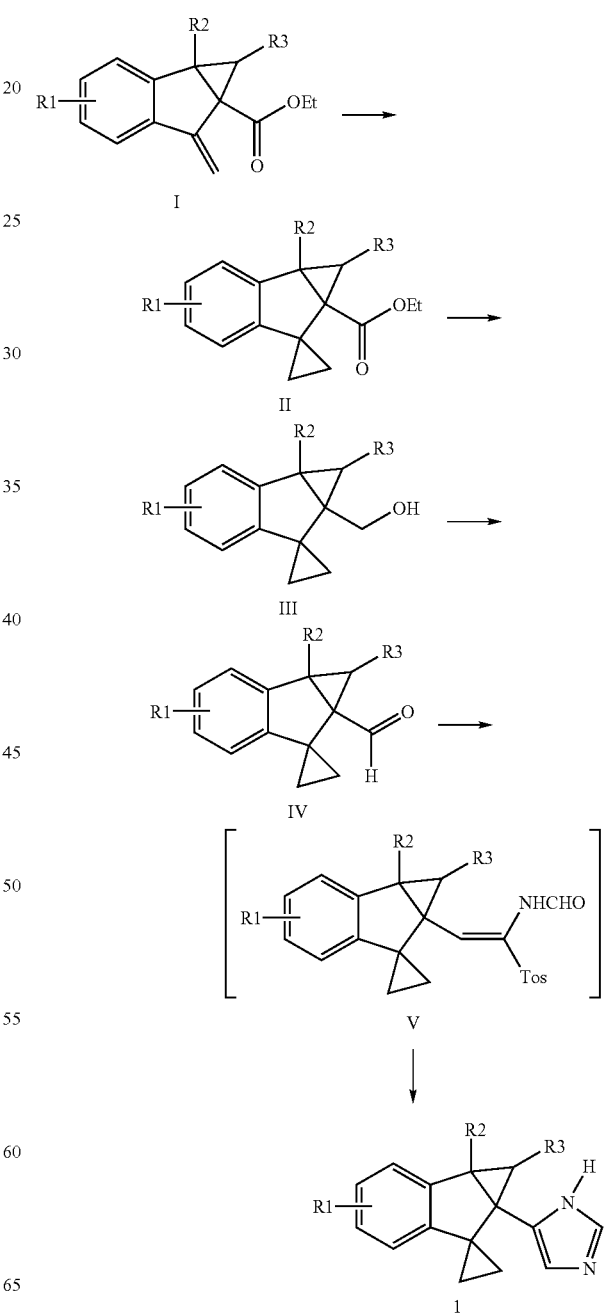

The preparation of the compounds according to the invention uses, as raw materials, the suitably substituted derivatives according to formula I, the synthesis method of which is described in the French patent application No. 0201839. A cyclopropanation reaction of the double bond, produced using a similar technique to that reported in Angew. Chem. Int. Ed. 2000, 39(24), 4539-42, results in the spiro derivative according to formula II. The ester function of the compound according to formula II is then reduced into the alcohol according to formula II by means of lithium borohydride in tetrahydrofuran according to a conventional organic chemistry method. The primary alcohol III is oxidised into the aldehyde according to formula IV by means of sulphur trioxide pyridine complex. The aldehyde IV is converted into the imidazole expected from formula 1, either in one step according to the method described in Heterocycles 1994, 39(1), 139-53; or via tosyl-formylamine according to formula V according to the method reported in Recl. Trav. Chim. Pays Bas 1979, 98(5), 258-62.

The invention also relates to pharmaceutical formulations containing, as the active ingredient, at least one of the derivatives according to general formula 1 or one of its salts or hydrates of its salts in combination with one or more inert substrates or other pharmaceutically acceptable vehicles.

The pharmaceutical formulations according to the invention may be, for example, formulations for oral, nasal, sublingual, rectal or parenteral administration. Examples of formulations for oral administration include tablets, capsules, granules, powders and solutions or oral suspensions.

The formulations suitable for the selected form of administration are known and described for example, in: Remington, The Science and Practice of Pharmacy, 19$^{th}$ edition, 1995, Mack Publishing Company.

The effective dose of a compound according to the invention varies according to numerous parameters such as, for example, the administration route selected, the weight, age, sex, state of progression of the disease to be treated and the susceptibility of the subject to be treated. As a result, the optimal dosage should be determined, according to the parameters deemed relevant, by the specialist in the field. Although the effective doses of a compound according to the invention may vary in wide proportions, the daily doses could range between 0.01 mg and 100 mg per kg of body weight of the subject to be treated. However, a daily dose of a compound according to the invention between 0.10 mg and 50 mg per kg of body weight of the subject to be treated is preferred.

The pharmaceutical formulations according to the invention are useful in the treatment of neurodegenerative diseases.

EXAMPLES

The following examples illustrate the invention, but do not limit it in any way.

In the examples and reference examples below:

(i) the progress of the reactions is monitored by means of thin layer chromatography (TLC) and, as a result, the reaction times are only mentioned as an indication;

(ii) different crystalline forms may give different melting points, the melting points reported in the present application are those of the products prepared according to the method described and are not corrected;

(iii) the structure of the products obtained according to the invention is confirmed by the nuclear magnetic resonance (NMR) and infrared (IR) spectra and centesimal analysis, the purity of the end products is verified by TLC, the enantiomeric purity of the reaction intermediates and the end products is determined by chiral phase HPLC;

(iv) the NMR spectra are recorded in the solvent specified. The chemical shifts (δ) are expressed in parts per million (ppm) with reference to tetramethylsilane. The multiplicity of the signals is specified by: s, singlet; d, doublet; t, triplet; q, quadruplet; m, multiplet; l, large.

(v) the different symbols of the units have their usual meaning: μg (microgram); mg (milligram); g (gram); ml (milliliter); mV (milliVolt); ° C. (degrees Celsius); mmole (millimole); nmole (nanomole); cm (centimeter); nm (nanometer); min (minute); ms (millisecond), Hz (hertz); [α](specific rotatory power measured at 589 nm, 25° C. and at the concentration c, in the present invention the dimension deg.cm$^2$.g$^{-1}$ is always understood); pressures are given in millibar (mb);

(vi) the abbreviations have the following meaning: F (melting point); Eb (boiling point); AUC (area under the curve);

(vii) the term "ambient temperature" refers to a temperature between 20° C. and 25° C.

Example 1

(6-spiro-1'-cyclopropane-1a,6-dihydro-1H-cyclopropa[a]inden-6a-yl)-ethyl carboxylate II-1

In the solution of 24.5 g (0.124 mole) of 2,4,6-trichlorophenol and 300 ml of dichloromethane under stirring and in nitrogen at −40° C., 113 ml (0.124 mole) of a toluene ZnEt$_2$ (1.1M) solution is added drop by drop. After 15 minutes of stirring at −40° C., 10 ml (0.124 mole) of diiodomethane is added and kept under stirring for 15 minutes before adding 6-methylene-1a,6-dihydro-1H-cyclopropa[a]inden-6a-ethyl carboxylate I-1, 13.22 g (0.062 mole). The suspension obtained is kept under stirring at ambient temperature overnight. After adding dichloromethane until completely dissolved, the solution is washed twice with 1N HCl followed by Na$_2$SO$_4$ and 0.5N NaOH (twice) and saline solution. The organic phase is dried on MgSO$_4$, filtered and the solvent is eliminated in a vacuum. The oil obtained is purified by silica gel chromatography using cyclohexane with 2% ethyl acetate as the eluent.

Yield: 89.8%

C$_{15}$H$_{16}$O$_2$: 228.29

$^1$H NMR (CDCl$_3$): 0.88 (m, 1H); 0.92 (m, 2H); 1.23 (t, 3H); 1.29 (m, 1H); 1.81 (dd, 1H); 2.35 (m, 1H); 3.17 (dd, 1H); 4.10 (d, 2H); 6.56 (m, 1H); 7.07 (m, 2H); 7.25 (m, 1H).

$^{13}$C NMR (CDCl$_3$): 14.15; 14.47; 17.16; 27.47; 29.21; 34.09; 34.16; 60.22; 118.97; 122.76; 125.40; 126.43; 142.46; 147.45; 171.84.

Example 2

(6-spiro-1'-cyclopropane-1a,6-dihydro-1H-cyclopropa[a]inden-6a-yl)-methanol III-1

The suspension of 13 g (0.234 mole) of KBH$_4$, 10.5 g (0.239 mole) of LiCl and 100 ml of anhydrous THF is kept under stirring at ambient temperature for 1 hour. To this suspension, the solution of 12.71 g (0.056 mole) of (6-spiro-1'-cyclopropane-1a,6-dihydro-1H-cyclopropa[a]inden-6a-yl)-ethyl carboxylate II-1 in 70 ml of anhydrous THF is added drop by drop and then reflux-heated under stirring for 4 hours. The suspension is vacuum-concentrated and the residue is treated with water. The product is extracted twice with ethyl acetate. The organic phase is washed with saline solution, dried on MgSO$_4$, filtered and vacuum-concentrated. The unprocessed oil is purified by silica gel chromatography using cyclohexane with 20% ethyl acetate as the eluent.

Yield: 85%

$C_{13}H_{14}O$: 186.25

$^1$H NMR (CDCl$_3$): 0.64 (t, 1H); 0.96 (m, 2H); 1.17 (m, 2H); 1.25 (t, 1H, exchangeable with D$_2$O); 1.54 (m, 1H); 2.49 (q, 1H); 3.56 (dd, 1H, (d, after exchange with D$_2$O)); 3.74 (dd, 1H, (d, after exchange with D$_2$O)); 6.58 (m, 1H); 7.06 (m, 2H); 7.25 (m, 1H).

Example 3

(6-spiro-1'-cyclopropane-1a,6-dihydro-1H-cyclopropa[a]inden-6a-yl)-carboxaldehyde IV-1

In the solution of 1.2 g (6.44 mmoles) of (6-spiro-1'-cyclopropane-1a,6-dihydro-1H-cyclopropa[a]inden-6a-yl)-methanol III-1 and 6 ml of anhydrous DMSO, 2.7 ml (19.4 mmoles) of triethylamine is added. The mixture obtained is placed under stirring on a chilled water bath and pyridine-SO$_3$ complex is added in 3.1 g (19.4 mmoles) fractions. After 4 hours of stirring at ambient temperature, the solution is poured into chilled water. The product is extracted twice with ethyl acetate. The organic phase is washed with an aqueous citric acid solution and then with saline solution. After drying on MgSO$_4$ and filtration, the solvent is eliminated at reduced pressure. The residual oil obtained is used without any other purification in the subsequent step.

$C_{13}H_{12}O$: 184.23

$^1$H NMR (CDCl$_3$): 0.97-1.03 (m, 2H); 1.15 (t, 1H); 1.23 (m, 1H); 2.01 (dd, 1H); 2.37 (m, 1H); 3.15 (dd, 1H); 6.62 (d, 1H); 7.12 (m, 2H); 7.26 (t, 1H); 9.26 (s, 1H).

Example 4

4-(6-spiro-1'-cyclopropane-1a,6-dihydro-1H-cyclopropa[a]inden-6a-yl)-1H-imidazole 1-1

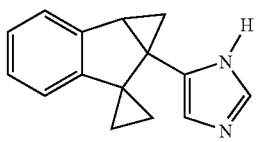

In the suspension of 1.18 g (6.4 mmoles) of (6-spiro-1'-cyclopropane-1a,6-dihydro-1H-cyclopropa[a]inden-6a-yl)-carboxaldehyde IV-1, 1.25 g (6.4 mmoles) of para-tolylsulfonylmethyl isocyanide and 15 ml of absolute ethanol under stirring at ambient temperature, 40 mg of sodium cyanide is added. After 1 hour of stirring at ambient temperature, the majority of the ethanol is eliminated at reduced pressure. To the residue, 20 ml of methanol ammonia (4N) solution is added and the solution obtained is maintained at 90° C. for 16 hours. After returning to ambient temperature, the brown solution obtained is heated to dryness at reduced pressure. The residue is taken up with ethyl acetate and the insolubles are filtered. The mother liquors are extracted twice with 1N hydrochloric acid. The acidic aqueous phase are washed with ether and then alkalinised. The product is extracted twice with ethyl acetate. The organic phases are washed with saline solution, dried on MgSO$_4$, filtered and the solvent is eliminated at reduced pressure. The residue is purified by silica chromatography using chloroform with 3% methanol as the eluent.

Yield: 28.8%

$C_{15}H_{14}N_2$: 222.28

Fumarate of compound in title, F: 218-220° C.

Elementary analysis, $C_{19}H_{18}N_2O_4$: 338.36 Calculated: C, 67.45%, H, 5.36%, N, 8.28%. Found: C, 67.17%, H, 5.36%, N, 8.15%.

$^1$H NMR (DMSOd$_6$): 0.61 (t, 1H); 0.79 (m, 2H); 0.94 (m, 1H); 1.09 (m, 1H); 1.46 (dd, 1H); 2.71 (dd, 1H); 6.62 (s, 2H); 6.68 (m, 1H); 6.90 (s, 1H); 7.06 (m, 2H); 7.28 (m, 1H); 7.63 (s, 1H).

The compounds according to formula 1-1 are split by liquid chromatography on CHIRALCEL OD substrate.

Example 5

(+)-4-(6-spiro-1'-cyclopropane-1a,6-dihydro-1H-cyclopropa[a]inden-6a-yl)-1H-imidazole (+)-(1-1)

Fumarate of compound in title, F: 168-170° C.

$[\alpha]^{25}_D$=+50.5°(c=0.334, CH$_3$OH)

Elementary analysis, $C_{19}H_{18}N_2O_4$: 338.36 Calculated: C, 67.45%, H, 5.36%, N, 8.28%. Found: C, 67.24%, H, 5.39%, N, 8.12%.

Example 6

(−)-4-(6-spiro-1'-cyclopropane-1a,6-dihydro-1H-cyclopropa[a]inden-6a-yl)-1H-imidazole (−)-(1-1)

Fumarate of compound in title, F: 170-172° C.

$[\alpha]^{25}_D$=−47.75° (c=0.295, CH$_3$OH)

Elementary analysis, $C_{19}H_{18}N_2O_4$: 338.36 Calculated: C, 67.45%, H, 5.36%, N, 8.28%. Found: C, 67.23%, H, 5.36%, N, 8.16%.

Example 7

4-(1-exo-methyl-6-spiro-1'-cyclopropane-1a,6-dihydro-1H-cyclopropa[a]inden-6a-yl)-1H-imidazole 1-2

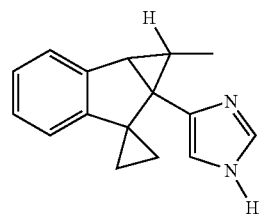

Using 1-exo-methyl-6-methylene-1a,6-dihydro-1H-cyclopropa[a]inden-6a-ethyl carboxylate I-2 as the starting product and following the procedure described in examples 1-4, the compound in the title is obtained.

Fumarate of compound in title, F: 203-205° C.

Elementary analysis, $C_{20}H_{20}N_2O_4$: 352.39 Calculated: C, 68.17%, H, 5.72%, N, 7.95%. Found: C, 68.69%, H, 5.90%, N, 8.07%.

¹H NMR (DMSOd₆): 0.57 (m, 1H); 0.65 (m, 1H); 0.88 (s, 3H); 0.92 (m, 1H); 1.28 (m, 1H); 2.54 (d, 1H, J=1.6 Hz); 6.61 (s, 2H); 6.63 (m, 1H); 6.68 (s, 1H); 7.04 (m, 2H); 7.28 (m, 1H); 7.66 (s, 1H).

Example 8

4-(1-endo-ethyl-6-spiro-1'-cyclopropane-1a,6-dihydro-1H-cyclopropa[a]inden-6a-yl)-1H-imidazole 1-3

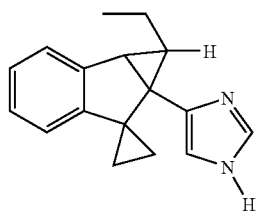

Using (1-endo-ethyl-6-methylene-1a,6-dihydro-1H-cyclopropa[a]inden-6a-ethyl carboxylate I-3, itself obtained from (Z)-2-(1-butenyl)-benzoic acid (RN 129780-54-7), as the starting product and following the procedure described in examples 1-4, the compound in the title is obtained.

Fumarate of compound in title, F: 179-181° C.

Elementary analysis, $C_{21}H_{22}N_2O_4$: 366.42 Calculated: C, 68.84%, H, 6.05%, N, 7.64%. Found: C, 68.36%, H, 5.99%, N, 7.63%.

¹H NMR (D₂O): 0.62 (m, 1H); 0.86 (t, 3H); 0.95 (m, 2H); 1.14 (m, 1H); 1.20 (m, 1H); 1.38 (m, 1H); 1.74 (m, 1H); 3.03 (d, 1H, J=8.8 Hz); 6.66 (s, 2H); 6.75 (m, 1H); 7.21 (m, 2H); 7.31 (s, 1H); 7.39 (m, 1H); 8.56 (s, 1H)

Example 9

4-(1a-methyl-6-spiro-1'-cyclopropane-1a,6-dihydro-1H-cyclopropa[a]inden-6a-yl)-1H-imidazole 1-4

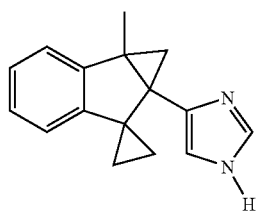

Using (1a-methyl-6-methylene-1a,6-dihydro-1H-cyclopropa[a]inden-6a-yl)-ethyl carboxylate I-4, itself obtained from 2-isopropenyl benzoic acid (RN 3609-46-9), as the starting product and following the procedure described in examples 1-4, the compound in the title is obtained.

Example 10

4-(4-fluoro-6-spiro-1'-cyclopropane-1a,6-dihydro-1H-cyclopropa[a]inden-6a-yl)-1H-imidazole 1-5

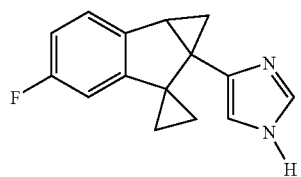

Using (4-fluoro-6-methylene-1a,6-dihydro-1H-cyclopropa[a]inden-6a-yl)-ethyl carboxylate I-5 as the starting product and following the procedure described in examples 1-4, the compound in the title is obtained.

Fumarate of compound in title, F: 214-216° C.

Elementary analysis, $C_{19}H_{17}N_2FO_4$: 356.35 Calculated: C, 64.04%, H, 4.811, N, 7.86%. Found: C, 63.87%, H, 4.88%, N, 7.81%.

¹H NMR (DMSOd₆): 0.60 (t, 1H); 0.83 (m, 2H); 0.98 (m, 1H); 1.09 (m, 1H); 1.42 (dd, 1H); 2.68 (dd, 1H); 6.56 (d, 1H); 6.66 (s, 2H); 6.83 (m, 1H); 6.88 (s, 1H); 7.27 (m, 1H); 7.59 (m, 1H).

The compounds according to formula 1 and their therapeutically acceptable salts offer properties of pharmacological interest.

The results of the tests are given in the table below:

| Compound | Affinity (pKi) Alpha-2A | Intrinsic activity % stimulated | Scopolamine memory deficiency % amplitude of effect (dose, mg/kg i.p.) |
|---|---|---|---|
| 1-1 | 9.5 | +14 | +122 (2.5) |
| (−)-adrenaline | — | +100 | — |
| Donepezil | — | — | +67 (0.16) |

Bonds with alpha-2 Adrenergic Receptors

The C6 cell membranes continuously expressing the human alpha-2A receptor are prepared in Tris-HCl (pH=7.6). The bond tests are conducted with 2 nM [₃H]RX 821002. The incubation medium consists of 0.4 ml of cell membranes (10 μg of proteins), 0.05 ml of radioligand and 0.05 ml of test product or phentolamine (10 μM) to determine the non-specific bond. The reaction is stopped after 30 minutes of incubation at 25° C. by adding 3 ml of Tris-HCl, 50 mM (pH=7.6), cold, followed by filtration on Whatman filters, GF/B using a Brandel. The Ki values are calculated according to the equation $Ki=IC_{50}/(1+C/Kd)$ where C is the concentration and Kd the dissociation constant, pKi=−logKi. Under these conditions, the compounds according to the invention appear to have a strong affinity for human alpha-2A adrenergic subtype receptors.

Measurement of alpha-2 Adrenergic Receptor Activation

The GTPγS responses are produced on membrane preparations in 20 mM HEPES (pH=7.4) with 30 μM of GDP, 100 mM of NaCl, 3 mM of MgCl₂ and 0.2 mM of ascorbic acid. The maximum GTPγS stimulation is determined in the presence of 10 mM of (−)-adrenaline and calculated with respect to the basal GTPγS response. The results are expressed with reference to adrenaline or RX 811059. Under these conditions, the compounds according to the invention are distinguished from the majority of the compounds according to the prior art in that they behave more like reverse agonists on human alpha-2A adrenergic receptors (see table above).

Scopolamine-induced Memory Deficiency Test.

Scopolamine has amnesiac properties in animals and humans. In this way, its administration to healthy humans induces certain symptoms similar to those observed in Alzheimer's disease. Therefore, the scopolamine-induced memory deficiency is used as an experimental pharmacological model of the memory disorders observed in the course of this condition. Scopolamine reduces acquisition, memorisation and recall capacities in a passive avoidance test in rats. It consists of measuring the hesitancy, after learning, shown by an animal to enter a dark compartment in which it receives a low-intensity electric shock. The administration of scopolamine does away with this hesitancy and the compounds studied inhibit the effect of scopolamine. The experimental protocol used is described in Psychopharmacol. 1992, 106, 26-30.

The compounds according to the invention show a high activity (see table above). The amplitude of the effect obtained with the compounds according to the invention is greater than that, for example, of donezepil, an acetylcholinesterase inhibitor used in clinical practice for the treatment of Alzheimer's disease (Chem. Rec. 2001, 1(1), 63-73). Therefore, the compounds according to the invention are capable of effectively inhibiting the memory deficiency induced by scopolamine.

Therefore, the results of the tests demonstrate that the compounds according to the formula 1:

have a strong affinity for human alpha-2A subtype adrenergic receptors;

generally behave as partial agonists or antagonists or reverse agonists on human alpha-2A adrenergic receptors;

are active, in vivo, in an animal model considered to be representative of the memory disorders observed in the course of Alzheimer's disease.

For this reason, the compounds according to their invention and their therapeutically acceptable salts are potentially useful as medicinal products, particularly in the treatment of some progressive neurodegenerative diseases, such as Alzheimer's disease, for example.

The compounds according to the invention may be administered by the oral, nasal, sublingual, rectal or parenteral route. As a non-limitative example of a formulation, a preparation of the compounds according to the invention is given below. The ingredients and other therapeutically acceptable substances may be introduced in other proportions without modifying the scope of the invention. The terms 'active ingredient' used in the formulation example below refer to a compound according to formula 1 or an addition salt or, if applicable, an addition salt of the compound according to formula 1 with a pharmaceutically acceptable mineral acid or organic acid.

Example of Pharmaceutical Formulation

Preparation formula for 1000 tablets each containing 10 mg of active ingredient consisting of at least one imidazolic compound according to the invention:

| | |
|---|---|
| Active ingredient | 10 g |
| Lactose | 100 g |
| Cornstarch | 10 g |
| Magnesium stearate | 3 g |
| Talc | 3 g |

What is claimed is:

1. A method of treating a memory deficiency in a subject in need of such treatment where the memory deficiency is associated with Alzheimer's disease, said method comprising administering to said subject an effective amount of a compound of formula (1):

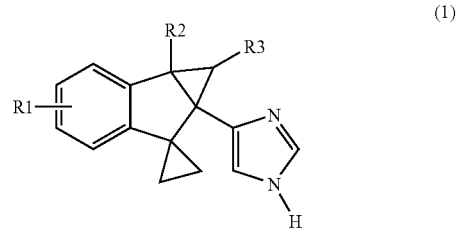

wherein:
R1 represents a hydrogen atom, a fluorine atom or a methoxyl group ($OCH_3$), the substituent R1 on the aromatic carbocycle occupying the position 2, 3, 4 or 5;
R2 represents a hydrogen atom or a methyl group;
R3 represents a hydrogen atom, a methyl group or an ethyl group;
or an addition salt thereof with a pharmaceutically acceptable mineral acid or organic acid, or enantiomers, diastereoisomers or tautomer thereof.

2. The method according to claim 1, wherein said memory deficiency is correlated with a memory deficiency induced by scopolamine.

3. A method of treating a memory deficiency in a subject in need of such treatment where the memory deficiency is associated with Alzheimer's disease, said method comprising administering to said subject an effective amount of at least one compound selected from the group consisting of:

4-(6-spiro-1'-Cyclopropane-1a,6-dihydro-1H-cyclopropa[a]inden-6a-yl)-1H-imidazole;

4-(2-fluoro-6-spiro-1'-cyclopropane-1a,6-dihydro-1H-cyclopropa[a]inden-6a-yl) -1H-imidazole;

4-(3-fluoro-6-spiro-1'-cyclopropane-1a,6-dihydro-1H-cyclopropa[a]inden-6a-yl) -1H-imidazole;

4-(4-fluoro-6-spiro-1'-cyclopropane-1a,6-dihydro-1H-cyclopropa[a]inden-6a-yl) 1H-imidazole;

4-(5-fluoro-6-spiro-1'-cyclopropane-1a,6-dihydro-1H-cyclopropa[a]inden-6a-yl) -1H-imidazole;

4-(1-exo-methyl-6-spiro-1'-cyclopropane-1a,6-dihydro-1H-cyclopropa[a]inden-6a-yl)-1H-imidazole;

4-(1-exo-methyl-2-fluoro-6-spiro-1'-cyclopropane-1a,6-dihydro-1H-cyclopropa [a]inden-6a-yl)-1H-imidazole;

4-(1-exo-methyl-3-fluoro-6-spiro-1'-cyclopropane-1a,6-dihydro-1H-cyclopropa [a]inden-6a-yl)-1H-imidazole;

4-(1-exo-methyl-4-fluoro-6-spiro-1'-cyclopropane-1a,6-dihydro-1H-cyclopropa [a]inden-6a-yl)-1H-imidazole;

4-(1-exo-methyl-5-fluoro-6-spiro-1'-cyclopropane-1 a,6-dihydro-1H-cyclopropa [a]inden-6a-yl)-1H-imidazole;

4-(1-endo-ethyl-6-spiro-1'-cyclopropane-1a,6-dihydro-1H-cyclopropa[a]inden-6 a-yl)-1H-imidazole; and 4-(1a-methyl-6-spiro-1'-cyclopropane-1a,6-dihydro-1H-cyclopropa[a]inden-6a-yl) -1H-imidazole;

and the addition salts thereof with pharmaceutically acceptable mineral acids or organic acids, and enantiomers, diastereoisomers and tautomers thereof.

4. The method according to claim 3, wherein said memory deficiency is correlated with a memory deficiency induced by scopolamine.

5. The method according to claim 3, wherein said at least one compound is selected from the group consisting of:

4-(6-spiro-1'-Cyclopropane-1a,6-dihydro-1H-cyclopropa[a]inden-6a-yl)-1H-imidazole;

(-)-4-(6-spiro-1'-Cyclopropane-1a,6-dihydro-1H-cyclopropa[a]inden-6a-yl)-1H-imidazole;

4-(4-fluoro-6-spiro-1'-cyclopropane-1a,6-dihydro-1H-cyclopropa[a]inden-6a-yl)-1H-imidazole; and 4-(1-exo-methyl-6-spiro-1'-cyclopropane-1a,6-dihydro-1H-cyclopropa[a]inden-6 a-yl)-1H-imidazole.

6. The method according to claim 5, wherein said memory deficiency is correlated with a memory deficiency induced by scopolamine.

7. The method according to claim 3, wherein said at least one compound is 4-(6-spiro-1'-Cyclopropane-1a,6-dihydro-1H-cyclopropa[a]inden-6a-yl)-1H-imidazole.

8. The method according to claim 7, wherein said memory deficiency is correlated with a memory deficiency induced by scopolamine.

9. The method according to claim 1, wherein the R3 and 1H-imidazole substituents of formula (1) occupy syn-periplanar positions with reference to the plane defined by the cyclopropanic nucleus, wherein R1 and R2 are as defined in claims 1, and R3 is a methyl group ($CH_3$) or an ethyl group ($CH_2CH_3$).

10. The method according to claim 1, wherein the R3 and 1H-imidazole substituents of formula (1) occupy anti-periplanar positions with reference to the plane defined by the cyclopropanic nucleus, wherein R1 and R2 are as defined in claim 1, and R3 is a methyl group ($CH_3$) or an ethyl group ($CH_2CH_3$).

11. The method according to claim 1, wherein the compound of formula (1) is the levogyral enantiomer or the dextrogyral enantiomer.

12. The method according to claim 3, wherein at least one compound selected from the group of compounds is the levogyral enantiomer or the dextrogyral enantiomer.

13. The method according to claim 9, wherein at least one compound selected from the group of compounds is the levogyral enantiomer or the dextrogyral enantiomer.

* * * * *